(12) United States Patent
Hibst et al.

(10) Patent No.: US 6,514,278 B1
(45) Date of Patent: Feb. 4, 2003

(54) METHOD AND DEVICE FOR THE SUPERFICIAL HEATING OF TISSUE

(75) Inventors: Raimund Hibst, Erbach (DE); Werner Falkenstein, Starnberg (DE)

(73) Assignee: Carl Baasel Lasertechnik GmbH (DE)

( * ) Notice: Subject to any disclaimer, the term of this patent is extended or adjusted under 35 U.S.C. 154(b) by 0 days.

(21) Appl. No.: 09/700,691

(22) PCT Filed: May 28, 1999

(86) PCT No.: PCT/EP99/03720

§ 371 (c)(1), (2), (4) Date: Dec. 6, 2000

(87) PCT Pub. No.: WO99/61105

PCT Pub. Date: Dec. 2, 1999

(30) Foreign Application Priority Data

May 28, 1998 (DE) .................................. 198 23 947

(51) Int. Cl.⁷ .............................................. A61B 18/18
(52) U.S. Cl. ............................. 607/89; 606/9; 606/11; 606/12; 606/3
(58) Field of Search .................. 607/88, 89; 606/9, 606/10, 11, 12, 13, 15, 16, 3, 7, 2

(56) References Cited

U.S. PATENT DOCUMENTS

| | | | | |
|---|---|---|---|---|
| 4,950,266 A | * | 8/1990 | Sinofsky | 606/2 |
| 5,196,004 A | * | 3/1993 | Sinofsky | 606/3 |
| 5,312,396 A | * | 5/1994 | Feld et al. | 606/11 |
| 5,843,073 A | * | 12/1998 | Sinofsky | 606/10 |
| 6,146,376 A | * | 11/2000 | Hack | 606/13 |
| 6,159,203 A | * | 12/2000 | Sinofsky | 606/7 |
| 6,159,204 A | * | 12/2000 | Hibst | 606/10 |
| 6,193,711 B1 | * | 2/2001 | Conners et al. | 606/12 |
| 6,306,130 B1 | * | 10/2001 | Anderson et al. | 607/88 |
| 6,364,872 B1 | * | 4/2002 | Hsia et al. | 606/9 |
| 6,425,873 B1 | * | 7/2002 | Marchitto et al. | 607/89 |

FOREIGN PATENT DOCUMENTS

| | | |
|---|---|---|
| EP | 0763371 | 3/1997 |
| EP | 9737723 | 10/1997 |
| WO | 9824514 | 6/1998 |

* cited by examiner

Primary Examiner—Teresa Walberg
Assistant Examiner—Fadi H. Dahbour
(74) Attorney, Agent, or Firm—Ostrolenk, Faber, Gerb & Soffen, LLP

(57) ABSTRACT

The invention relates to a method and a device for the superficial heating of tissue by means of a pulsed light source. According to the invention a series of light pulses is applied to the tissue surface. The first part of this series is configured such that the tissue surface and, by heat conduction, tissue areas situated below the tissue surface are rapidly heated to a defined target temperature without tissue removal. The subsequent part of the series results in oscillation of the temperature of the tissue areas located below the tissue surface around a value which is slightly lower than the target temperature.

18 Claims, 1 Drawing Sheet

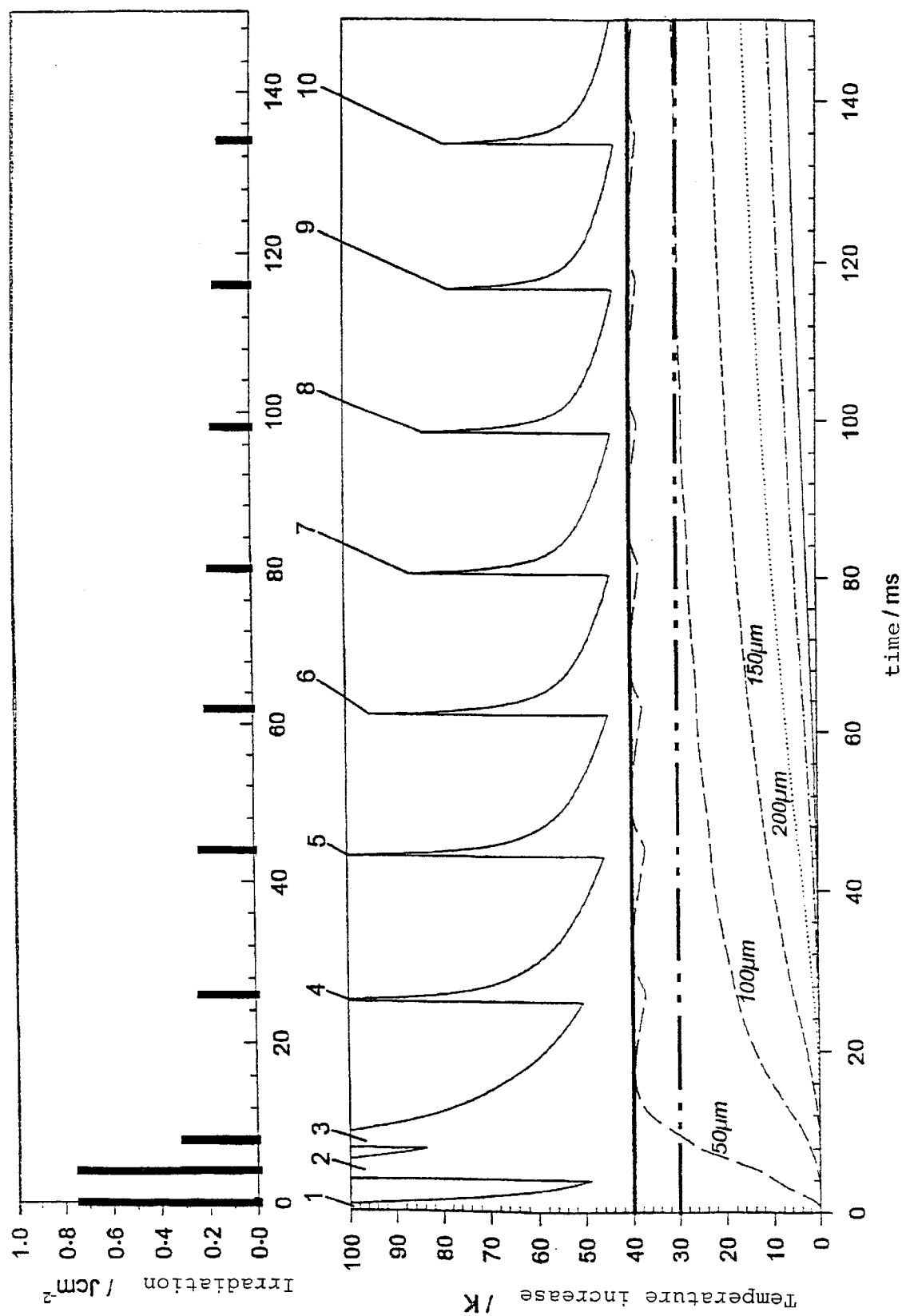

METHOD AND DEVICE FOR THE SUPERFICIAL HEATING OF TISSUE

The invention relates to a method and device for the superficial heating of tissue of the type stated in the preamble of patent claims 1 and 11, respectively.

For the removal of lines and smoothing of prematurely aged skin (for example due to excessive exposure to sun), for some time laser systems such as the Er:YAG and $CO_2$ lasers have been successfully used in dermatology as an alternative to chemical peeling. With these lasers, the skin is superficially removed. In a way similar to in the case of peeling, both the smoothing effect and the probability of undesired side-effects (scars, hyper- or hynopigmentation) increase with the depth of removal from approximately 60 μm (superficial removal) to 0.8 mm (deep peeling). The removal can have the effect of partly leveling the surface of the skin, and a tightening is observed. According to current literature, the skin-tightening effect is explained by the fact that harmful, elastotic layers of skin are removed and, in the course of the subsequent healing of the wound, are replaced by a repair layer with new collagen of the type I. This effect is in principle independent of the way in which the skin was removed or irreversibly changed; it explains why mechanical dermabrasion, chemical agents or laser-induced ablations are equally effective.

The heat-induced shrinkage of collagen is discussed as a further mode of action, existing only in the case of lasers. Type I collagen fibrils shrink when heated to a temperature range between 55° C. to 60° C. and 70° C. (beginning of coagulation) to a third of their length, without becoming biologically inactive. This is a process commencing immediately with the heating. Fitzpatrick et al. presume this effect to be a cause of the immediate tightening of loose and lined skin unexpectedly observed during "resurfacing" (R. E. Fitzpatrick et al, Pulsed Carbon Dioxide Laser Resurfacing of Photoaged Facial Skin, Arch Dermatol 132, 395–402, 1996).

Although "resurfacing" based on skin removal. is effective in many cases, it also has adverse side-effects. The most important are:

postoperative risk of infection (in some cases coverage of the entire face with film is required for several days)

erythema lasting for several weeks restricted social life for at least a week possible hyperpigmentation, less commonly hypopigmentation.

Furthermore, the newly formed skin shows deviations with respect to its structure in comparison with the remaining skin.

With the existing smoothing of lines using $CO_2$ and Er:YAG lasers, the removal and new formation of skin are presumably the main factors determining the result. This hypothesis is made plausible by the extent of the depth of the layers of skin treated: the regions of removed skin (approximately 100 μm) and irreversibly damaged, coagulated skin ($CO_2$ laser approximately 80 to 100 μm, Er:YAG laser approximately 40 μm) undergo the mechanism of new skin formation. For the collagen shrinkage, on the other hand, only the region adjacent to the coagulation zone is available, lying in the temperature interval between the coagulation temperature of approximately 70° C. and the lower limit of the collagen shrinkage temperature of approximately 55° C. to 60° C. For both lasers, this regionlis relatively thin in the extent of its depth during the skin removal, so that an appreciable contribution to the smoothing cannot be expected, though it is estimated to be greater in the case of $CO_2$ lasers than, for example, in the case of Er:YAG lasers.

WO-A-97 37723 discloses a method and device of the type stated at the beginning in which the laser wavelength is chosen with respect to the thickness of the target tissue and the spectral absorption coefficients of this wavelength such that the laser radiation reaches the collagen layer in the depth of the skin without experiencing any significant absorption in the layers of skin lying above. The surface of the skin may in this case be cooled before the laser radiation is applied, in order to avoid impairment of the surface of the skin by the possible slight absorption in the upper skin. In this case, the selection of laser is restricted to certain laser wavelengths because of the required great depth of penetration into the tissue.

EP-A2-0 763 371 discloses a method and apparatus for skin rejuvenation and wrinkle smoothing in which ablation takes place by means of an Er:YAG laser, a flashlamp additionally being used to produce light pulses in the range of 600–1000 nm for heating up the collagen. The Er:YAG laser merely brings about ablation of the surface on account of the small depth of penetration of the light pulses, while the flashlamp has a greater depth of penetration and reaches the collagen. The heating of the collagen by the Er:YAG laser is obviously not regarded as adequate. For this reason, the Er:YAG laser is used in the customary way merely for removing the upper layers of skin.

The invention is based on the object of providing a method and device of the type stated at the beginning which permit improved elimination of skin damage or skin impairments, such as for example scars, lines and the like.

This object is achieved by the features specified in patent claims 1 and 11, respectively.

Advantageous refinements and developments of the invention emerge from the subclaims.

In the case of the method and device according to the invention, the heating extends from the surface of the skin, in which the absorption substantially takes place, over a relatively great layer thickness beneath the surface of the skin, it being possible in a preferred refinement of the invention to dispense completely with removal in many cases. In other cases, it may be advisable to use a combination of local removal (for example line ridges) and heating over a large region.

The range of problems so far discussed with respect to lines also apply in a similar way to the treatment of scars. In principle, renewed damage to the surface of the skin should be minimized here. A targeted heat-induced shrinkage of (scar) collagen is also possible in this case.

According to a preferred refinement of the method and device, various types of laser light sources may be used as the light source, such as for example a Ho:YAG laser, an Er:YAG laser, an Er:YSGG laser, a Tm:YAG laser, a $CO_2$ laser or an Nd:YAG laser, these only being some examples.

In the case of all types of light sources, a considerable amount of energy can be introduced into the tissue beneath the surface of the skin by the pulse control according to the invention.

In this case, the energy level is chosen such that there is no removal, but adequate heating of the deeper-lying collagen layer is obtained by heat conduction.

The invention is explained in more detail below on the basis of an exemplary embodiment represented in the drawing.

Represented in the upper half of the drawing is a series of light pulses, with energy densities of the individual pulses preselected such that the temperature profiles at the surface of the skin and in the layers of tissue lying beneath the surface of the skin, at depths of 50 μm, 100 μm, 150 μm and 200 μm, represented in the lower part of the illustration are obtained over time. The vertical scale indicates the temperature difference ΔT in °K. with respect to the temperature of the skin.

As the drawing reveals, in the case of the example represented, a series of laser pulses 1 to 10 are applied to the surface of the skin, the first pulses of the series, for example pulses 1 and 2, preferably having a higher energy level, energy density or power, which however must lie below the removal threshold, in order to achieve rapid heating initially of the surface of the skin and then, after a time delay, heating of the desired layer of tissue lying beneath it by heat conduction to the target temperature. As the curve for a depth of 50 μm reveals, this causes the temperature at this depth to increase relatively rapidly and then be maintained as uniformly as possible at a desired difference from the target temperature of, for example, 40° K. As can be seen, the temperature for the curve for a depth of 50 μm drops slightly again after application of the three first light pulses and is then for example raised again to the desired limit temperature by the pulse represented at 4. The same also applies to the subsequent pulses 5 to 10, which in each case bring about reheating to the target temperature. The pulses of the pulse series following the first pulses may in this case have a lower energy level, brought about by a lower power and/or duration, since the energy required for maintaining the desired target temperature is lower. The temperature at the depth of 100 μm and in the deeper-lying layers of 150 μm and 200 μm in this case increases continuously and approaches a desired limit value of a temperature difference of, for example, 30° K for the depth of 100 μm.

According to an advantageous refinement of the invention, the temperature at the surface of the skin, and if appropriate in layers lying beneath it, can be monitored, for example by a surface temperature sensor, so that a corresponding pulse control of the individual pulses can take place, it being ensured, for example, that the prescribed target temperature, for example of irreversible thermal damage, is never exceeded.

With lower requirements for a rapid heating-up time, a pulsed laser can of course equally be clock-controlled with a constant pulse series frequency and pulse energy level or pulse energy density or pulse power below the ablation threshold, backed up if appropriate by measurement of the surface temperature of the skin, so that comparable temperature increases can be achieved.

The device according to the invention permits targeted treatment of the skin by appropriate control of the pulse series and energy levels of individual pulses, it being possible for these energy levels and pulse durations or pulse intervals to be chosen according to the desired application.

The device according to the invention can not only be used for the thermal changing of collagen fibrils, but can serve generally for the purpose of inducing physiologically specific temperature increases.

For example, to increase the enzyme activity in the skin, it is merely necessary to induce a temperature increase of a few °K. To deactivate enzymes, layers of tissue lying beneath the surface of the skin should be heated to a temperature of approximately 43° C. to 55° C. For shrinkage of collagen without coagulation, temperatures in the range from approximately 55° C. to 60° C. and 70° C. should be used, for coagulation the temperature range is 70° C. to 100° C.

If the method and device according to the invention are to be used for superficially changing hard tissues (bone, [to]oth enamel), the temperature increase should be several 100 K.

If desired, the pulse series represented in the drawing may be followed by a subsequent removal pulse of higher power.

If the method and device according to the invention are to be used for the removal of malignant or bacterially or virally contaminated tissue, the method according to the invention reduces the risk of entraining living tumor cells, bacteria or viruses by the possibility of performing a coagulation before the removal.

In the case of a specific example, corresponding to the drawing, a number of pulses of an Er:YAG laser with a total energy level of approximately 100 mJ was used (cf. table). With 56 mJ altogether, the first three pulses in this case contain over half the total energy, these pulses following relatively quickly one after the other. This leads to rapid heating of the surface to the permitted target temperature increase of ΔT=40° K at a depthL of 50 μm. The subsequent pulses 4 to 10 serve simply for stabilizing this temperature. For this stabilization, increasingly lower individual pulse energy levels are subsequently required, it being possible for there to be relatively long pauses between the individual pulses. In this way, virtually stable gradients are then achieved in deeper layers of tissue, as can be seen from the curves for a depth of 100 μm or 150 μm and 200 μm at the end of the ten pulses.

TABLE

| Pulse number | 1 | 2 | 3 | 4 | 5 | 6 | 7 | 8 | 9 | 10 |
|---|---|---|---|---|---|---|---|---|---|---|
| Energy/mJ | 23.3 | 23.3 | 9.4 | 7.2 | 6.9 | 6.0 | 5.3 | 4.7 | 4.4 | 4.4 |
| Irradiation/Jcm$^{-2}$ | 0.74 | 0.74 | 0.30 | 0.23 | 0.22 | 0.19 | 0.17 | 0.15 | 0.14 | 0.13 |
| Time interval from the previous pulse/ms | — | 4 | 4 | 18 | 18 | 19 | 19 | 18 | 18 | 18 |

This laser and the pulse series merely represent a preferred exemplary embodiment, without any restriction.

There is, for example, also the possibility of using a laser with a high pulse frequency, for example 50 Hz, which is additionally controlled, if appropriate, by a sensor measuring the temperature of the surface of the skin.

What is claimed is:

1. A method for the superficial heating of tissue with the aid of a pulsed light source, in which method a series of light pulses are applied to the surface of the tissue, wherein a light source with a wavelength of which the light is absorbed mainly in the region at the surface of the skin which lies above a tissue depth of 50 μm is used, wherein a first part of the series of light pulses is configured such that rapid heating of the surface of the skin and then, after a time delay, heating of regions of tissue lying beneath this region of the surface of the skin to a prescribed target temperature is achieved by heat conduction without tissue removal, and wherein a subsequent part of the series brings about an oscillation of the temperature of the regions of tissue about a value lying slightly below the target temperature.

2. The method as claimed in claim 1, wherein the pulse energy levels or pulse energy densities of the pulses following the first part of the series and/or the interval between the subsequent pulses is dimensioned such that only slight deviations from the target temperature occur.

3. The method as claimed in claim 1, wherein the energy level, energy density or power of the individual pulses lies close to the removal threshold for tissue, but below it.

4. The method as claimed in claim 1, wherein the pulses following the first part of the series have such an energy level, energy density or power and are at such intervals as to compensate for the cooling of the surface caused by the heat conduction.

5. The method as claimed in claim 1, wherein a measurement of the surface temperature serves for controlling the energy levels of individual pulses of the subsequent part of the series.

6. The method as claimed in claim 5, wherein the measurement of the surface temperature takes place radiometrically.

7. The method as claimed in claim 1, wherein the light source uses an Er:YAG or Er:YSGG laser material.

8. The method as claimed in one claim 1, wherein the light source is a $CO_2$ laser.

9. A device for the superficial heating of biological tissue, with a light source which can be activated in a pulsed manner and a control unit for controlling the light source, which activates the light source in such a way that series of light pulses each of a prescribed duration and irradiation intensity are supplied, wherein the light source supplies light pulses of such a wavelength that the light pulses are mainly absorbed in a region at the surface of the skin which lies above a tissue depth of 50 $\mu$m, wherein each series comprises a first part, which brings about rapid heating of this region of the surface of the skin and then, after a time delay, heating of regions of tissue lying beneath this region of the surface of the skin by heat conduction to a prescribed target temperature, which lies below the temperature at which the tissue removal occurs, and a subsequent part, which brings about an oscillation of the temperature of the surface of the skin and/or of the region of tissue lying beneath the surface of the skin about the target temperature, this temperature likewise lying below a temperature inducing removal.

10. The device as claimed in claim 9, wherein the device has a measuring instrument for measuring the surface temperature, and wherein the output signal of the measuring instrument activates the control unit.

11. The device as claimed in claim 10, wherein the measuring instrument is a radiometric measuring instrument.

12. The device as claimed in claim 1, wherein the control unit controls the light source in such a way that the subsequent part of the or each series is followed by a pulse of a higher energy level, energy density or power, which brings about a removal of tissue.

13. The device as claimed in claim 12, wherein the first part of the series brings about rapid heating up to a target temperature between the coagulation temperature and the removal temperature, while the subsequent part of the pulse series brings about an enlargement of the coagulation zone, and wherein the removal pulse is dimensioned such that a small seam of the coagulated tissue remains.

14. The device as claimed in claim 9, wherein a temperature increase, to a temperature of less than 43° C., which brings about an increase in the enzyme activity in the skin is achieved with the first part and the subsequent part of the pulse series.

15. The device as claimed in claim 9, wherein a temperature increase, to a temperature in the range of 43° C. to 55° C., which brings about a deactivation of enzymes is achieved with the first part and the subsequent part of the pulse series.

16. The device as claimed in claim 9, wherein a temperature increase, to a temperature in the range of 55° C. to 70° C., which brings about a shrinkage of collagen without coagulation is achieved with the first part and the subsequent part of the pulse series.

17. The device as claimed in claim 9, wherein the light source uses an Er:YAG or Er:YSGG laser material.

18. The device as claimed in claim 9, wherein the light source is a $CO_2$ laser.

* * * * *